United States Patent
Bramer et al.

(10) Patent No.: US 6,180,811 B1
(45) Date of Patent: Jan. 30, 2001

(54) REDUCING LOW MOLECULAR WEIGHT CYCLIC ORGANOSILOXANES IN A RECIRCULATING PROCESS STREAM

(75) Inventors: David Harold Bramer, Hanover, IN (US); Larry Herbert Wood, Campbellsburg, KY (US)

(73) Assignee: Dow Corning Corporation, Midland, MI (US)

( * ) Notice: Under 35 U.S.C. 154(b), the term of this patent shall be extended for 0 days.

(21) Appl. No.: 09/218,245

(22) Filed: Dec. 22, 1998

(51) Int. Cl.[7] ........................................ C07F 7/08
(52) U.S. Cl. ........................ 556/460; 556/462; 556/467
(58) Field of Search ................................. 556/460, 462, 556/467

(56) References Cited

U.S. PATENT DOCUMENTS

| | | | |
|---|---|---|---|
| 3,714,213 | 1/1973 | Miller et al. | 260/448.2 |
| 4,197,251 | 4/1980 | Hirakawa et al. | 556/460 |
| 4,895,967 | 1/1990 | Crivello et al. | 556/451 |
| 5,196,559 | * 3/1993 | Schulz, Jr. et al. | 556/460 |
| 5,247,116 | 9/1993 | Buese et al. | 556/460 |
| 5,395,956 | 3/1995 | Haines et al. | 556/451 |

FOREIGN PATENT DOCUMENTS

0738732A2   10/1996   (EP) ........................... C07F/7/21

* cited by examiner

Primary Examiner—Porfirio Nazario-Gonzalez
(74) Attorney, Agent, or Firm—Melvin D. Fletcher

(57) ABSTRACT

A process for continuously reducing the amount of cyclic organosiloxane in a recirculating process stream. The process comprises washing a process stream in a wash step to reduce chloride content of the process stream, distilling the process stream into a low-boiling fraction comprising low molecular weight cyclic organosiloxanes and an inert solvent and a high-boiling fraction comprising linear organosiloxanes and high molecular weight cyclic organosiloxanes, and reequilibrating the overhead low-boiling fraction in the presence of a reequilibration catalyst to form a reequilibration mixture comprising high molecular weight cyclic organosiloxanes and the inert solvent, and recycling the reequilibration mixture to the wash step.

16 Claims, No Drawings

REDUCING LOW MOLECULAR WEIGHT CYCLIC ORGANOSILOXANES IN A RECIRCULATING PROCESS STREAM

BACKGROUND OF INVENTION

The present invention is a process for continuously reducing the amount of low molecular weight cyclic organosiloxane in a recirculating process stream. The process comprises washing a process stream in a wash step to reduce chloride content of the process stream, distilling the process stream into a fraction comprising low molecular weight cyclic organosiloxanes and an inert solvent and a high-boiling fraction comprising linear organosiloxanes and high molecular weight cyclic organosiloxanes and reequilibrating the low-boiling fraction in the presence of a reequilibration catalyst to form a reequilibration mixture comprising high molecular weight cyclic organosiloxanes and the inert solvent, and recycling the reequilibration mixture to the washing step.

Dimethyldichlorosilane generally contains small amount of heptane as a by-product of the direct process. When the dimethyldichlorosilane is hydrolyzed to form polysiloxanes the by-product heptane remains as an unwanted odor causing contaminant. The heptane is subsequently removed by passing the hydrolyzate through a distillation column where the hydrolyzate is recovered as a high-boiling bottom stream and a low-boiling overhead stream comprising heptane and lower boiling siloxanes are recycled back into the process. The low boiling siloxanes which consists mostly of hexamethylcyclotrisiloxane is recycled back into the process and as a consequence builds up over time to as much as one-quarter to one-third of the recycle stream. As the hexamethylcyclotrisiloxane content of the recycle stream increases, it significantly impacts the capacity of the column used to remove heptane from the hydrolyzate. As a result of hexamethylcyclotrisiloxane build-up, additional capital is required to make the column large enough to handle the recycled hexamethylcyclotrisiloxane. When the recycle streams' hexamethylcyclotrisiloxane concentration becomes too great, the recycle stream must be removed from the process for disposal as a hazardous waste. Therefore, a process is needed to remove hexamethylcyclotrisiloxane from the recycle stream, while allowing the heptane to be recycled.

Haines et al., U.S. Pat. No. 5,395,956, describe a process for preparing cyclic organohydrogensiloxanes by contacting an organohydrogendichlorosilane with about a stoichiometric equivalent of water to form a hydrolyzate. The hydrolyzate is diluted in an inert solvent and contacted with an acidic rearrangement catalyst to effect formation of cyclic organohydrogensiloxanes. The cyclic organohydrogensiloxanes are separated from the inert solvent and linear organohydrogensiloxanes and the linear organohydrogensiloxanes are then recycled to the process for further contact with the acidic rearrangement catalyst.

Miller et al., U.S. Pat. No. 3,714,213, describe a process for preparing cyclic methylhydrogensiloxanes by contacting linear methylhydrogen siloxanes with an acid catalyst absorbed on a carrier. The process requires the presence of high molecular weight chain termination groups. The yield of tetramethylcyclotetrasiloxane is reported to be about 73 percent.

Crivello et al., U.S. Pat. No. 4,895,967, describe a method for making cyclic organohydrogensiloxanes by contacting a linear organohydrogensiloxane with a heated bed of a cracking catalyst at reduced pressure. The resulting volatile cyclic organohydrogensiloxane is recovered. A typical yield for the method is reported to be about 85 percent.

The present inventors have discovered that hexamethylcyclotrisiloxane can be removed from a process recycle stream to eliminate hexamethylcyclotrisiloxane build-up and the solvent recycled back to the process. The present invention provides a process for continuously removing hexamethylcyclotrisiloxane from a recirculating process stream and passing it through a reequilibration reactor containing a catalyst to reequilibrate the hexamethylcyclotrisiloxane to higher molecular weight cyclic organosiloxanes.

SUMMARY OF INVENTION

The present invention is a process for continuously reducing the amount of low molecular weight cyclic organosiloxane in a recirculating process stream. The process comprises washing a process stream in a wash step to reduce chloride content of the process stream, distilling the process stream into a low-boiling fraction comprising low molecular weight cyclic organosiloxanes and an inert solvent and a high-boiling fraction comprising linear organosiloxanes and high molecular weight cyclic organosiloxanes, and reequilibrating the low-boiling fraction in the presence of a reequilibration catalyst to form a reequilibration mixture comprising high molecular weight cyclic organosiloxanes and the inert solvent, and recycling the reequilibration mixture to the wash step.

DESCRIPTION OF INVENTION

The present invention is a continuous process for reducing the amount of low molecular weight cyclic organosiloxane in a recirculating process stream. The process comprises:

(A) washing a process stream in a wash step to reduce chloride content of the process stream, (B) distilling the process stream into a low-boiling fraction comprising low molecular weight cyclic organosiloxanes described by formula $(R_2SiO)_n$ and an inert solvent and a high-boiling fraction comprising linear organosiloxanes and high molecular weight cyclic organosiloxanes described by formula $(R_2SiO)_m$, (C) reequilibrating the low-boiling fraction in the presence of a reequilibration catalyst to form a reequilibration mixture comprising high molecular weight cyclic organosiloxanes and the inert solvent, and (D) recycling the reequilibration mixture to the wash step, where each R is independently selected from the group consisting of saturated monovalent hydrocarbon radicals comprising one to about 12 carbon atoms and an aryl radical, n is less than 5, and m is 4 to 14.

The process stream of the present process is formed by reacting silanes with water to form a hydrolysis mixture. The silanes useful in the process may be a single species of silane as described by formula $R_2SiCl_2$ or a mixture of such silanes. R is selected from a group consisting of saturated monovalent hydrocarbon radicals comprising one to about 12 carbon atoms and aryl radicals. R can be, for example, methyl, ethyl, propyl, isopropyl, butyl, tertiary butyl, sec-butyl, hexyl, cyclohexyl, dodecyl, phenyl, tolyl, and naphtyl. Preferred is when R is selected from the group consisting of methyl and phenyl. Most preferred is when R is methyl. The preferred silane is dimethyldichlorosilane.

In the hydrolysis process the silane is contacted with about 1000% to 2000% excess of the stoichiometric equivalent of water in a hydrolysis reactor forming a hydrolysis mixture comprising cyclic and linear organosiloxanes and hydrogen chloride.

The cyclic organosiloxanes formed by the hydrolysis process are described by formulas $(R_2SiO)_n$, and $(R_2SiO)_m$ and the linear organosiloxanes are described by formula $HO(R_2SiO)_qH$, where R is as previously defined, n is less than 5, m=4 to 14 and q=2 to 50. Examples of cyclic siloxanes are hexamethylcyclotrisiloxane ($D_3$), octamethylcyclotetrasiloxane ($D_4$), and dodecamethylcyclohexasiloxane. Examples of linear siloxanes are 1,3-dihydroxytetramethyldisiloxane, 1,5-dihydroxyhexamethyltrisiloxane, and 1,7-dihydroxyoctamethyltetrasiloxane.

The hydrolysis mixture is phase separated into a phase comprising the cyclic and linear organosiloxanes and a phase comprising aqueous hydrogen chloride. An inert solvent is added to the hydrolysis mixture to facilitate phase separation. By the term "inert" it is meant a solvent which can serve as a diluent and does not otherwise have significant reaction in the process. Examples of suitable inert solvents are hydrocarbons, such as, hexane, heptane, benzene, toluene, xylene, THF, and diethyl ether. The preferred solvent is heptane. The amount of solvent useful in the separation process is 20 about 2 to 15 weight percent based on the weight of the hydrolysis mixture. Preferred is about 5 to 10 weight percent on the same basis.

The inert solvent increases the density difference between the cyclic and linear organosiloxanes and the hydrogen chloride such that within the phase separator, the hydrolysis mixture separates by gravity into an upper process stream comprising the cyclic and linear organosiloxanes and inert solvent and a lower aqueous hydrogen chloride layer. The lower aqueous hydrogen chloride layer is withdrawn and recycled back to the hydrolysis process.

In the present process, the process stream as described above is water washed by passing the process stream through a wash step. By adding water to the process stream, the hydrogen chloride becomes soluble in the water forming an upper organosiloxane and solvent phase and a lower hydrogen chloride acid phase. The lower hydrogen chloride acid phase is removed form the process stream and recycled back to the hydrolysis process. The chloride content of the process stream is reduced to about 100 ppm. The washing step may be repeated to further reduce the process stream chloride content to about 0.5 ppm.

After washing, the process stream is distilled into a low-boiling fraction comprising low molecular weight cyclic organosiloxanes described by formula $(R_2SiO)_n$ and the inert solvent and a high-boiling fraction comprising linear organosiloxanes and high molecular weight cyclic organosiloxanes described by formula $(R_2SiO)_m$, where each R is independently selected from the group consisting of saturated monovalent hydrocarbon radicals comprising one to about 12 carbon atoms and an aryl radical, n is less than 5, and m is 4 to 14. The low molecular weight cyclic organosiloxanes consist mostly of hexamethylcyclotrisiloxane and smaller amounts of octamethylcyclotetrasiloxane. The high-boiling fraction is withdrawn from the distillation column and collected in a suitable container.

The low-boiling fraction comprising the low molecular weight cyclic organosiloxanes and inert solvent distilled from the process stream are passed through a reequilibration reactor containing a reequilibration catalyst to reequilibrate the low molecular weight cyclic organosiloxanes forming a reequilibration mixture comprising high molecular weight cyclic organosiloxanes described by formula $(R_2SiO)_m$, where R and m are as previously defined.

The amount of inert solvent remaining in the low-boiling fraction of the process stream is about 20 to 95 weight percent based on the weight of the low-boiling fraction of the process stream. For use in the present process, it is preferred that the inert solvent comprise about 30 to 90 weight percent of the low-boiling fraction of the process stream. Most preferred is when the inert solvent comprises about 60 to 85 weight percent of the low-boiling fraction of the process stream.

The reequilibration catalysts useful in the present process are catalysts, such as, trifluoromethane sulfonic acid, HCl activated clays, sulfuric acid activated clays, and sulfonic acid ion exchange resins, such as, sulfonated divinylbenzenestyrene copolymer resin. Contact of the catalyst with the low-boiling fraction can be effected by standard means for contacting liquids with solids, for example, in a fixed-bed, a stirred-bed, or a fluid-bed reactor. The process can be run as a continuous, semi-continuous, or batch process. Preferred is when the present process is run as a continuous process using a fixed-bed of the reequilibration catalyst.

The low-boiling fraction comprising the low molecular weight cyclic organosiloxanes are contacted with a reequilibration catalyst which facilitates reequilibration of the lower boiling cyclic siloxanes, such as, hexamethylcyclotrisiloxane and octamethylcyclotetrasiloxane into a mixture of high molecular weight cyclic organosiloxanes comprising a reequilibration mixture. The high molecular weight cyclic organosiloxanes can then be removed from the process during distillation. The reequilibration mixture comprising the high molecular weight cyclic organosiloxanes and inert solvent are recycled back to the wash step.

The following examples are provided to illustrate the present invention. The examples are not intended to limit the present claims.

EXAMPLE 1

Evaluation of the reequilibration of hexamethylcyclotrisiloxane and octamethylcyclotetrasiloxane using trifluoromethane sulfonic acid as a catalyst. A 10 ml sample comprising 26 weight percent hexamethylcyclotrisiloxane, 13 weight percent octamethylcyclotetrasiloxane, and 61 wt % heptane was placed in a glass vial. About 15 drops of trifluoromethane sulfonic acid was added to the vial. The vial was closed, shaken, and allowed to sit for about 2 hours. An aliquot of the original sample and the reequilibrated sample were analyzed by gas chromatography (GC) using a 15 thermal conductivity detector (TCD) and the results are reported in Table 1.

TABLE 1

| Component | Before Reequilibration wt % | After Reequilibration wt % |
| --- | --- | --- |
| D3 | 26 | 0 |
| D4 | 13 | 18 |
| D5 |  | 11 |
| D6 |  | 4 |
| D7 |  | 1 |
| D8 |  | 0.4 |
| D9 |  | 0.2 |
| D10 |  | 0.2 |

EXAMPLE 2

Evaluation of the reequilibration of hexamethylcyclotrisiloxane and octamethylcyclotetrasiloxane using an Amberlyst® A-15 resin bead catalyst bed. A catalyst bed was prepared by pouring Amberlyst® A-15 resin beads, Rohm and Haas, Philadelphia, Pa., into a glass tube having a catalyst bed 2 cm in diameter and 13 cm high. A sample comprising 22.3 weight percent of hexamethylcyclotrisiloxane, 11.7 weight percent of octamethylcyclotetrasiloxane, and 61 wt % heptane was passed through the catalyst bed into a receiving vessel. After passing through the catalyst bed, the sample was analyzed by GC-TCD and passed through the catalyst bed again. This procedure was repeated six times with GC-TCD being conducted after each pass. The residence time of the sample in the catalyst bed was about 5 minutes per pass. The results of the analysis are reported in Table 2 in wt %.

TABLE 2

| Component | Initial Sample | Pass 1 | Pass 2 | Pass 3 | Pass 4 | Pass 5 | Pass 6 | Pass 7 |
|---|---|---|---|---|---|---|---|---|
| D3 | 22.3 | 3.9 | 0.2 | 0.1 | 0.2 | 0.2 | 0 | 0 |
| D4 | 11.7 | 12.2 | 11.3 | 11 | 10.8 | 10.6 | 10.4 | 10.6 |
| D5 | | 4.2 | 5.9 | 6.9 | 7.2 | 7.1 | 7.1 | 7.2 |
| D6 | | 2.5 | 2.7 | 2.7 | 2.5 | 2.5 | 2.4 | 2.5 |
| D7 | | 0.4 | 0.6 | 0.7 | 0.7 | 0.7 | 0.7 | 0.7 |
| D8 | | 0.2 | 0.2 | 0.3 | 0.3 | 0.3 | 0.3 | 0.3 |
| D9 | | 0.1 | 0.2 | 0.2 | 0.2 | 0.2 | 0.2 | |
| D10 | | | 0.1 | 0.1 | | 0.1 | | |
| D11 | | | 0.1 | | | | | |
| D12 | | | 0.1 | | | | | |
| D13 | | | 0.1 | | | | | |

We claim:

1. A continuous process for reducing the amount of low molecular weight cyclic organosiloxane in a recirculating process stream comprising, (A) washing a process stream in a wash step to reduce chloride content of the process stream, (B) distilling the process stream into a low-boiling fraction comprising low molecular weight cyclic organosiloxanes described by formula $(R_2SiO)_n$ and an inert solvent and a high-boiling fraction comprising linear organosiloxanes and high molecular weight cyclic organosiloxanes described by formula $(R_2SiO)_m$, (C) reequilibrating the low-boiling fraction in the presence of a reequilibration catalyst to form a reequilibration mixture comprising high molecular weight cyclic organosiloxanes and the inert solvent, and (D) recycling the reequilibration mixture to the wash step, where each R is independently selected from the group consisting of saturated monovalent hydrocarbon radicals comprising one to about 12 carbon atoms and an aryl radical, n is less than 5, and m is 4 to 14.

2. A process according to claim 1, where the inert solvent is heptane.

3. A process according to claim 1, where the reequilibration catalyst is a sulfonated divinylbenzenestyrene copolymer resin.

4. A process according to claim 1, where the reequilibration catalyst is trifluoromethane sulfonic acid.

5. A process according to claim 1, where the low molecular weight cyclic organosiloxanes comprises hexamethylcyclotrisiloxane and octamethylcyclotetrasiloxane.

6. A process according to claim 1, where the amount of inert solvent in the low-boiling fraction is about 20 to 95 weight percent based on the weight of the low-boiling fraction.

7. A process according to claim 1, where the amount of inert solvent in the low-boiling fraction is about 30 to 90 weight percent based on the weight of the low-boiling fraction.

8. A process according to claim 1, where the amount of inert solvent in the low boiling fraction is about 60 to 85 weight percent based on the weight of the low-boiling fraction.

9. A process according to claim 1, where chloride content of the process stream is between about 0.5 to 100 ppm.

10. A process for reducing the amount of low molecular weight cyclic organosiloxanes in a process stream comprising:

(A) contacting a process stream comprising a low molecular weight cyclic organosiloxane described by formula $(R_2SiO)_n$ and heptane with a reequilibration catalyst to effect formation of a high molecular weight cyclic organosiloxane described by formula $(R_2SiO)_m$, and (B) recovering the high molecular weight cyclic organosiloxane, where each R is independently selected from the group consisting of saturated monovalent hydrocarbon radicals comprising one to about 12 carbon atoms and aryl radicals, n is less than 5, and m is 4 to 14.

11. A process according to claim 10, where the reequilibration catalyst is a sulfonated divinylbenzenestyrene copolymer resin.

12. A process according to claim 10, where the reequilibration catalyst is trifluoromethane sulfonic acid.

13. A process according to claim 10, where the low molecular weight cyclic organosiloxanes comprises hexamethylcyclotrisiloxane and octamethylcyclotetrasiloxane.

14. A process according to claim 10, where the amount of inert solvent is about 20 to 95 weight percent based on the weight of the low molecular weight cyclic organosiloxane.

15. A process according to claim 10, where the amount of inert solvent is about 30 to 90 weight percent based on the weight of the low molecular weight cyclic organosiloxane.

16. A process according to claim 1, where the amount of inert solvent is about 60 to 85 weight percent based on the low molecular weight cyclic organosiloxane.

* * * * *